United States Patent [19]

Hsieh et al.

[11] Patent Number: 5,110,887
[45] Date of Patent: May 5, 1992

[54] SUPERABSORBENT CROSSLINKED AMPHOLYTIC ION PAIR COPOLYMERS

[75] Inventors: Henry L. Hsieh; Iqbal Ahmed, both of Bartlesville, Okla.

[73] Assignee: Phillips Petroleum Company, Bartlesville, Okla.

[21] Appl. No.: 761,572

[22] Filed: Sep. 18, 1991

Related U.S. Application Data

[63] Continuation of Ser. No. 607,005, Oct. 31, 1990.

[51] Int. Cl.$^5$ .............................................. C08F 12/30
[52] U.S. Cl. .................................. 526/287; 524/106; 526/303.1; 526/312; 526/342; 564/281; 564/291
[58] Field of Search ............ 526/287, 303.1, 312, 526/342; 564/281, 291; 524/106

[56] References Cited

U.S. PATENT DOCUMENTS

| | | | |
|---|---|---|---|
| 3,050,390 | 8/1962 | Levinos et al. | 96/35 |
| 3,478,001 | 11/1969 | Szita et al. | 260/79.3 |
| 4,251,651 | 2/1981 | Kawakami | 526/204 |
| 4,440,228 | 4/1984 | Swanson | 166/274 |
| 4,460,732 | 7/1984 | Buscall | 524/460 |
| 4,471,097 | 9/1984 | Uhl et al. | 526/240 |
| 4,644,020 | 2/1991 | Stahl | 522/79 |
| 4,647,617 | 3/1987 | Saotome | 524/733 |
| 4,666,964 | 5/1987 | Hunter et al. | 524/106 |
| 4,910,250 | 3/1990 | Saotome | 524/556 |

OTHER PUBLICATIONS

Salamone, J. C. et al. "Synthesis and Aqueous Solution Viscosity Behavior of Polyampholytes from Cataionic-Anionic Pair", *Adv. Chem.* Sec. 187 pp. 337-346.
Salamone, J. C. et al. "Aqueous Salt Absorption by Ampholytic Polysaccharides", Polymer, vol. 26, 1985.
Salamone, J. C. et al. "Acrylic Ampholytic Ionomers" Polymers, vol. 23, pp. 843, 898 (1982).
Salamone, J. C. et al. "Drag Reduction by Acrylic Copolymers" Current Topics in Polymer Science, vol. 1, edited by R. M. Ottenbrite et al., Hauser Publishers (1987), pp. 292-307.
Salamone, J. C. et al. "Behavior of Polyampholytes in Aqueous Salt Solution", ACS-Polymeric Materials Science and Engineering, vol. 55 (Fall 1986).
Salamone, J. C. et al. "Synthesis and Solution Properties of Ampholytic Acrylamide Ionomers" J. C. Macromol, Sci.-Chem. A25 (5-7) pp. 811-837 (1988).
Salamone, J. C. et al. "Polymerization of Ion-Pair Comonomers of Related Structures", J. Macromol, Sci.-Chem, A22 (5-7), pp. 653-664 (1985).
Salamone, J. C. et al. "Aqueous Solution Properties of a Poly (Vinyl Imidazolium Sulphobetaine)", Polymer, vol. 19, pp. 1757, 1978.

Primary Examiner—Joseph L. Schofer
Assistant Examiner—Fred Zitomer
Attorney, Agent, or Firm—Richmond, Phillips, Hitchcock & Umphlett

[57] ABSTRACT

The present invention provides an article of manufacture which contains a crosslinked ampolytic copolymer that is highly absorbent to aqueous electrolyte solutions. The articles of manufacture of the present invention contain copolymers formed by the copolymerization of an effective amount of each of the following components to produce a polymer which is highly absorbent to aqueous electrolyte solutions:

(a) an ampholytic ion pair monomer comprising
  (i) the ammonium cation 3-methacrylamidopropyldimethylammonium and
  (ii) a sulfonate anion selected from the group consisting of 2-acrylamido-2-methylpropane sulfonate, 2-methacryloyloxyethane sulfonate, vinyl sulfonate, styrene sulfonate and combinations of two or more thereof;

(b) at least one comonomer selected from the group consisting of acrylamide, methacrylamide, acrylonitrile, acrylic acid, methacrylic acid, alkali salts of acrylic acid, alkali salts of methacrylic acid, 3-methacrylamidopropyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and combinations of two or more thereof; and (c) at least one crosslinking agent which has at least two polymerizable olefinic functionalities wherein the olefinic functionalities are suitable for crosslinking.

The invention also provides a method of using the polymers of the present invention for absorbing aqueous electrolyte solutions comprising the step of contacting the polymers of the present invention with the aqueous electrolyte solution.

33 Claims, No Drawings

SUPERABSORBENT CROSSLINKED AMPHOLYTIC ION PAIR COPOLYMERS

This application is a continuation of application Ser. No. 07/607,005, filed Oct. 31, 1990, now pending, the text which is hereby incorporated by reference.

BACKGROUND OF THE INVENTION

1. Field of the Invention

This invention pertains to crosslinked superabsorbent copolymers formed from an ampolytic ion pair (3-methacrylamidopropyldimethylammonium (MPDMA) cation/sulfonate anion) copolymerized with other comonomers. A further aspect of the invention relates to a method of using the aforesaid crosslinked superabsorbent copolymers for absorbing aqueous electrolyte solutions.

2. Description of the Prior Art

Polymers for absorbing aqueous electrolyte solutions are used in numerous commercial and industrial applications. For example, polymers are used to improve the water absorbency of paper towels and disposable diapers.

Though known water absorbing polymers are highly absorbent to deionized water, they are dramatically less absorbent to aqueous electrolyte solutions such as salt water, brine, and urine. For example, hydrolyzed crosslinked polyacrylamide absorbs 1,024 grams of deionized water per gram of polymer, but only 25 grams of synthetic urine per gram of polymer. Crosslinked polyacrylate absorbs 423 grams of deionized water per gram of polymer, but only 10 grams of synthetic urine per gram of polymer. Hydrolyzed crosslinked polyacrylonitrile absorbs 352 grams of deionized water per gram of polymer, but only 25 grams of synthetic urine per gram of polymer.

It would be a valuable contribution to the art to develop polymers with high absorbency to aqueous electrolyte solutions such as tap water, salt water, brine, and urine. It also would be a valuable contribution to the art to develop inexpensive polymers with high absorbency to aqueous electrolyte solutions. The market for these types of polymers is large and the uses are numerous. Therefore, seemingly small improvements in the absorbency translate into large savings in the quantity of polymer required to absorb these aqueous electrolyte solutions and large savings to the consumer.

SUMMARY OF THE INVENTION

The polymers of the present invention comprise crosslinked polymers formed by the copolymerization of an effective amount of each of the following components to produce a highly absorbent polymer:
(a) an ampholytic ion pair monomer comprising
  (i) the ammonium cation 3-methacrylamidopropyldimethylammonium and
  (ii) a sulfonate anion selected from the group consisting of 2-acrylamido-2-methylpropane sulfonate, 2-methacryloyloxyethane sulfonate, vinyl sulfonate, styrene sulfonate and combinations of two or more thereof;
(b) at least one comonomer selected from the group consisting of acrylamide, methacrylamide, acrylonitrile, acrylic acid, methacrylic acid, alkali salts of acrylic acid, alkali salts of methacrylic acid, 3-methacrylamidopropyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and combinations of two or more thereof; and
(c) at least one crosslinking agent which has at least two polymerizable olefinic functionalities wherein each of the olefinic functionalities are suitable for crosslinking.

A further aspect of the invention relates to a method of absorbing an aqueous electrolyte solution comprising the step of contacting the polymers of the present invention with an aqueous electrolyte solution.

Thus, it is a general object of the present invention to provide the polymers of the present invention having improved absorbency to aqueous electrolyte solutions.

A further object of the present invention is to provide a method of using the polymers of the present invention for absorbing aqueous electrolyte solutions comprising the step of contacting the polymers of the present invention with the aqueous electrolyte solution.

Further objects, features, and advantages of the present invention will be readily apparent to those skilled in the art upon reading the description of the invention which follows.

DESCRIPTION OF THE INVENTION

The present invention provides polymers that are highly absorbent to aqueous electrolyte solutions. Typical aqueous electrolyte solutions include but are not limited to the group consisting of tap water, salt water, brine, and urine. The polymers of the present invention comprise polymers formed by the copolymerization of an effective amount of each of the following components to produce a polymer which is highly absorbent to aqueous electrolyte solutions:
(a) an ampholytic ion pair monomer comprising
  (i) the ammonium cation 3-methacrylamidopropyldimethylammonium (also referred to as MPDMA) and
  (ii) a sulfonate anion selected from the group consisting of 2-acrylamido-2-methylpropane sulfonate (also referred to as AMPS ® a trademark of Lubrizol), 2-methacryloyloxyethane sulfonate (also referred to as MES), vinyl sulfonate, styrene sulfonate and combinations of two or more thereof;
(b) at least one comonomer selected from the group consisting of acrylamide (also referred to as AM), methacrylamide, acrylonitrile (also referred to as AN), acrylic acid (also referred to as AA), methacrylic acid, alkali salts of acrylic acid (also referred to as X-AA), alkali salts of methacrylic acid, 3-methacrylamidopropyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and combinations of two or more thereof; and
(c) at least one crosslinking agent which has at least two polymerizable olefinic functionalities wherein each of the olefinic functionalities are suitable for crosslinking.

As used in this application, the term "alkali salts" is used generically, unless otherwise indicated, to mean alkali salts including but not limited to salts containing lithium, sodium, potassium, and ammonium cations.

As used in this application, the term "monomer" is used generically, unless otherwise indicated, to mean monomers, comonomers, termonomers, tetramonomers, etc. The term "comonomer" is used generically, unless otherwise indicated, to mean monomers, comonomers, termonomers, tetramonomers, etc. for polymers wherein there are at least two different monomers.

As used in this application, the term "polymer" is used generically, unless otherwise indicated, to mean homopolymers, copolymers, terpolymers, tetrapolymers, etc., and thus includes polymers prepared using any number of monomers. The term "copolymer" is used generically to mean polymers prepared using two or more different monomers.

As used in this application, the term "hydrolysis" is used generically, unless otherwise indicated, to include hydrolysis of nitrile functionalities and hydrolysis of amide functionalities. These hydrolysis reactions are loosely referred to in the art as "saponification." Hydrolysis of these functionalities may occur under acidic or basic conditions. Under basic hydrolysis conditions, the term may also include, unless otherwise indicated, neutralization of carboxylic acid and sulfonic acid functionalities.

The ampolytic ion pair monomer used in the present invention may be prepared by titrating an aqueous solution of a sulfonic acid monomer to pH 7 with 3-methacrylamidopropyldimethylamine at a temperature of about 0°-15° C. The resulting aqueous solution containing the ampholytic ion pair may be purified by contacting the aqueous solution one or more times with small quantities of activated charcoal. The concentration of the ampolytic ion pair in the aqueous solution may be determined by evaporatively drying a known amount of the aqueous solution and weighting the residue.

Alternatively the ampholytic ion pair monomer for use in the preparation of the present invention may be prepared by methods which are well known to those skilled in the art. For example, one of the ampholytic ion pair monomers can be prepared by reacting 3-methacrylamidopropyldimethylamine with commerically available 2-acrylamido-2-methylpropane sulfonic acid or 2-methacryloyloxyethane sulfonic acid in anhydrous tetrahydrofuran. See J. C. Salamone, C. C. Tsai, A. P. Olson, and A. C. Watterson, *Adv. Chemical Series*, Volume 187, pages 337-346.

The olefinic comonomers can include but are not limited to the group consisting of acrylamide, methacrylamide, acrylonitrile, acrylic acid, methacrylic acid, alkali salts of acrylic acid, alkali salts of methacrylic acid, 3-methacrylamidopropyldimethylamine, 2-acrylamido-2-methylpropane sulfonic acid, alkali salts of 2-acrylamido-2-methylpropane sulfonic acid, 2methacryloyloxyethane sulfonic acid, alkali salts of 2-methacryloyloxyethane sulfonic acid, N-vinyl-2-pyrrolidone and combinations of two or more thereof. All these suitable olefinic comonomers are believed to be commercially available.

Suitable crosslinking agents can include but are not limited to the group consisting of N,N-diallylmethacrylamide, diallylamine, N,N-bisacrylamidoacetic acid, N,N'-bisacrylamidoacetic acid methylester, N,N'-methylenebisacrylamide (methylene-bis-acrylamide), N,N-benzylidenebisacrylamide, allylacrylate, diisopropenylbenzene, diallyl succinate, ethylene glycol diacrylate, diallylacrylamide, divinylbenzene, and combinations of two or more thereof. All these suitable crosslinking agents are believed to be commercially available.

The polymers of the present invention were generally prepared by mixing the various monomers in the desired stoichiometric ratios in aqueous solution and then initiating the free-radical copolymerization. The copolymerization of the ampholytic ion pair monomer with the olefinic comonomer and crosslinking agent can be achieved by any of the well known free-radical polymerization techniques in solution, suspension, or emulsion environment. Well known azo compounds commonly employed to initiate free radical polymerization reactions include 2,2'-azobis(N,N'-dimethylisobutyramidine) dihydrochloride, azobisisobutyronitrile, 4,4'-azobis(4-cyanovaleric acid), 2,2'-azobis(2,4-dimethyl(4-methyoxyvaleronitrile), 2,2'-azobis(2,4-dimethylvaleronitrile), 2,2'-azobis(2-amidinopropane)-dihydrochloride, 2-t-butylazo-2-cyano-4-methoxy-4-methylpentane, and 2-t-butylazo-2-cyano-4-methylpentane, and 4-t-butylazo-4-cyanovaleric acid.

Well known inorganic peroxide compounds commonly employed to initiate free radical polymerization reactions include hydrogen peroxide, alkali metal persulfates, alkali metal perborates, alkali metal perphosphates, and alkali metal percarbonates. Well known organic peroxide compounds commonly employed to initiate free radical polymerization reactions include lauryl peroxide, 2,5-dimethyl-2,5-bis(2-ethylhexanoylperoxy)hexane, t-butylperoxypivilate, t-butylperoctoate, p-menthane hydroperoxide, and benzoylperoxide. The compound t-butylhyponitrile is a well known alkyl hyponitrite commonly employed to initiate free radical polymerization reactions. Furthermore, ultraviolet light is commonly employed to initiate free radical polymerization reactions. In addition, such other methods of copolymerization as would have occurred to one skilled in the art may be employed, and the present invention is not limited to the particular method of preparing the crosslinked polymer set out herein.

These inventive copolymers containing an olefinic comonomer with amide, nitrile, carboxylic acid, or sulfonic acid functionalities or crosslinking agent with amide, nitrile, carboxylic acid, or sulfonic acid functionalities can optionally be at least partially hydrolyzed and/or neutralized by heating with aqueous base such as aqueous sodium hydroxide or aqueous potassium hydroxide. The degree of hydrolysis and/or neutralization can be controlled by stoichiometrically limiting the amount of base relative to the amount of amide, nitrile, carboxylic acid, and sulfonic acid functionalities. If the hydrolysis is carried out under acidic conditions, the amide and nitrile functionalities can be converted to carboxylic acid functionalities without neutralizing the carboxylic acid or sulfonic acid functionalities of the polymer.

The broadest range for the compositions of the inventive crosslinked MPDMA/sulfonate copolymers is an effective amount of each of the ampholytic ion pair monomer, olefinic comonomer, and crosslinking agent to produce a polymer highly absorbent to aqueous electrolyte solutions.

The preferred ranges for the compositions of the inventive polymers given in Tables I, and II reflect the relative stoichiometric amount in mole percent based on the total number of moles of all the various monomers mixed together before the copolymerization. The actual composition of the polymers of the present invention produced by the copolymerization reaction may vary slightly from the stoichiometric mixture before the co-polymerization depending on the the reaction conditions.

The broad and preferred ranges for the compositions of the inventive crosslinked MPDMA/sulfonate copolymers are given in Table I. These broadly preferred ranges for the compositions of the present invention are based on the experimental data provided in Example V, Tables VIII and IX, for those polymer compositions which produce an absorbency of at least 70 gram of synthetic urine per gram of inventive crosslinked MPDMA/sulfonate copolymer.

TABLE I

| Broad Compositions For Inventive Polymers | | | | | |
|---|---|---|---|---|---|
| | MPDMA/ sulfonate | AM | AN | AA | X-AA | LINK |
| | MOLE PERCENT | | | | | |
| broad | 10-30 | 70-90 | — | — | — | 0.01-0.3 |
| preferred | 10-25 | 75-90 | — | — | — | 0.01-0.2 |
| broad | 3-25 | — | 65-97 | — | — | 0.01-0.3 |
| preferred | 5-25 | — | 75-95 | — | — | 0.01-0.2 |
| broad | 1-30 | — | — | — | 70-99 | 0.01-0.3 |
| preferred | 1-10 | — | — | — | 90-99 | 0.01-0.2 |
| broad | 1-20 | 10-25 | — | — | 55-89 | 0.01-0.3 |
| preferred | 1.5-15 | 10-20 | — | — | 65-88.5 | 0.01-0.2 |

MPDMA/sulfonate = 3-methacrylamidopropyldimethylammonium cation/a sulfonate anion selected from the group consisting of 2-acrylamido-2-methylpropane sulfonate, 2-methacryloyloxyethane sulfonate, and any combination therof
AM = Acrylamide
AN = Acrylonitrile
AA = Acrylic Acid
X-AA = Alkali Salt of Acrylic Acid (Acrylate)
LINK = Crosslinking Agent The more preferred and most preferred ranges for the compositions of the inventive crosslinked MPDMA/AMPS copolymers are given in Table II. These more preferred and most preferred ranges for the compositions of the present invention are based on the experimental data provided in Example V, Table VIII, for those polymer compositions which produce an absorbency of at least 70 gram of synthetic urine per gram of inventive MPDMA/AMPS polymer.

TABLE II

| Preferred Compositions For Inventive MPDMA/AMPS Polymers | | | | | | |
|---|---|---|---|---|---|---|
| | MPDMA/ AMPS | AM | AN | AA | X-AA | LINK |
| | MOLE PERCENT | | | | | |
| more preferred | 10-30 | 70-90 | — | — | — | 0.01-0.2 |
| most preferred | 10-25 | 75-90 | — | — | — | 0.01-0.1 |
| more preferred | 3-35 | — | 65-97 | — | — | 0.01-0.2 |
| most preferred | 5-25 | — | 75-95 | — | — | 0.01-0.1 |
| more preferred | 1-15 | — | — | — | 85-99 | 0.01-0.2 |
| most preferred | 1-10 | — | — | — | 90-99 | 0.01-0.1 |
| more preferred | 1.5-15 | 10-21 | — | — | 64-88.5 | 0.01-0.2 |
| most preferred | 6-10 | 10-15 | — | — | 75-84 | 0.01-0.1 |

MPDMA/AMPS = 3-methacrylamidopropyldimethylammonium cation/2-acrylamido-2-methylpropane sulfonate
AM = Acrylamide
AN = Acrylonitrile
AA = Acrylic Acid
X-AA = Alkali Salt of Acrylic Acid (Acrylate)
LINK = Crosslinking Agent

TABLE III

| Preferred Compositions For Inventive MPDMA/MES Polymers | | | | | | |
|---|---|---|---|---|---|---|
| | MPDMA/ MES | AM | AN | AA | X-AA | LINK |
| | MOLE PERCENT | | | | | |
| more preferred | 10-30 | 70-90 | — | — | — | 0.01-0.2 |
| most preferred | 10-25 | 75-90 | — | — | — | 0.01-0.1 |
| more preferred | 3-35 | — | 65-97 | — | — | 0.01-0.2 |
| most preferred | 5-25 | — | 75-95 | — | — | 0.01-0.1 |
| more preferred | 1-25 | — | — | — | 75-99 | 0.01-0.2 |
| most preferred | 1-6 | — | — | — | 94-99 | 0.01-0.1 |
| more preferred | 1.5-15 | 10-21 | — | — | 64-88.5 | 0.01-0.2 |
| most preferred | 6-10 | 10-15 | — | — | 75-84 | 0.01-0.1 |

MPDMA/AMPS = 3-methacrylamidopropyldimethylammonium cation/2-acrylamido-2-methylpropane sulfonate
AM = Acrylamide
AN = Acrylonitrile
AA = Acrylic Acid
X-AA = Alkali Salt of Acrylic Acid (Acrylate)
LINK = Crosslinking Agent A further aspect of the invention relates to a method of absorbing aqueous electrolyte solutions comprising the step of contacting the polymers of the present invention with the aqueous solution. Typical aqueous electrolyte solutions are not limited to but may be selected from the group consisting of tap water, salt water, brine, and urine. For the purpose of this invention tap water is defined to have an electrolyte concentration of less than 500 ppm of dissolved electrolytes, urine is defined to have an electolyte concentration of from greater than 500 ppm to at most 10,000 ppm of dissolved electrolytes, salt water is defined to have an electrolyte concentration from greater than 10,000 ppm to at most 34,000 ppm of dissolved electrolytes and brine is defined to have an electrolyte concentration of from greater than 34,000 ppm to the saturation point of the aqueous solution.

The following examples are intended to illustrate the advantages of this invention but are not intended to unduly limit this invention.

EXAMPLE I

The control data in Table IV demonstrates that although known polymers are highly absorbent to deionized water, they are dramatically less absorbent to aqueous electrolyte solutions such as salt water and urine. Known polymer compositions include crosslinked polyacrylamide, partially saponified crosslinked polyacrylamide, crosslinked polyacrylonitrile, partially saponified crosslinked acrylonitrile, crosslinked polyacrylic acid, neutralized crosslinked polyacrylic acid, crosslinked polyacrylate, and polymers thereof with sodium 2-acrylamido-2-methylpropane sulfonate. The best of these known polymers absorbs up to about 60 grams of urine per gram of polymer, and most of the known polymers absorb much less than 50 grams of urine per gram of polymer.

The polymers of the control data were prepared by mixing the monomers in the proportions given in Table VI in an aqueous solution of deionized water. The monomers were present in about 30-40 weight percent relative to the amount of deionized water. The free radical polymerization was initiated with commercially available 2,2'-azobis(N,N'-dimethylisobutyramidine) dihydrochloride. About 0.1 mole percent based on the total moles of the monomers of the azo free-radical initiator was employed. The reaction was then degassed by bubbling nitrogen gas through the mixture for 15 minutes. The reaction temperature was maintained between 20°-35° C. for 24 hours. The reactions produced transparent or cloudy hard gels of the crosslinked polymers. A large volume of deionized water was added to the polymer product and the polymers were allowed to swell for about 24 hours. The swelled polymers were dried in a forced convection oven at 150° F. The dried polymers were then mechanically blended to a powder.

a 100 mesh per inch stainless steel sieve. The absorbency was determined by weighing the isolated polymer containing the absorbed liquid and subtracting the weight of the dry polymer. The absorbency was measured in units of grams of liquid per grams of polymer. The synthetic urine was prepared by dissolving 0.64 gram $CaCl_2$, 1.14 gram $MgSO_4.7H_2O$, 8.20 gram NaCl, and 20.0 gram urea into 1000 gram deionized water. Several of the polymers were tested two or three times, and the experimental error was within plus or minus 2-5 percent. This small experimental error was largely caused by gel blocking and minor diffusion problems that prevented the aqueous liquid from contacting with all the polymer.

TABLE IV

| EXP # | AMPS ® | AM | AN | AA | Control Data X-AA | LINK mole ratio* | XOH | DIW g/g** | SU |
|---|---|---|---|---|---|---|---|---|---|
| | MOLE PERCENT | | | | | | | | |
| 126A | — | 100 | — | — | — | 0.05 | NO | 17 | 15 |
| 126 | — | 100 | — | — | — | 0.05 | YES | 1024 | 25 |
| 406R | — | 100 | — | — | — | 0.05 | YES | 364 | 40 |
| 125A | — | 100 | — | — | — | 0.20 | NO | 13 | 12.5 |
| 125 | — | 100 | — | — | — | 0.20 | YES | 295 | 16 |
| 26 | — | — | 100 | — | — | 0.05 | YES | 608 | 46 |
| 405 | — | — | 100 | — | — | 0.10 | NO | 0 | 0 |
| 405 | — | — | 100 | — | — | 0.10 | YES | 414 | 42 |
| 129 | — | — | 100 | — | — | 0.20 | YES | 352 | 25 |
| 127A | — | — | — | 100 | — | 0.20 | NO | 21 | 11 |
| 127 | — | — | — | 100 | — | 0.20 | Neutr. | 423 | 10 |
| 194 | — | — | — | — | 100(K) | 0.05 | NO | 669 | 57 |
| 204 | — | — | — | — | 100(Na) | 0.05 | NO | 505 | 41 |
| 211 | — | 13 | — | — | 87 | 0.05 | NO | — | 65 |
| 267 | 3 | 13 | — | — | 84 | 0.05 | NO | 350 | 38 |
| 372 | 3 | 20 | — | — | 77 | 0.05 | NO | 417 | 47 |
| 20 | 6 | 13 | — | — | 81 | 0.05 | NO | 738 | 56 |
| 21 | 6 | 26 | — | — | 68 | 0.05 | NO | 533 | 47 |
| 22 | 6 | — | — | — | 94 | 0.05 | NO | 488 | 55 |
| 23 | 10 | 13 | — | — | 77 | 0.05 | NO | 570 | 59 |
| 25 | 20 | 13 | — | — | 67 | 0.05 | NO | 624 | 62 |
| 19 | 99.95 | — | — | — | — | 0.05 | NO | Soluble | |

AMPS ® = 2-acrylamido-2-methylpropane sulfonate (Note AMPS is a trademark of Lubrizol.)
AM = Acrylamide
AN = Acrylonitrile
AA = Acrylic Acid
X-AA = Alkali Salt of Acrylic Acid (Acrylate)
LINK = Methylene-bis-acrylamide Crosslinking Agent
XOH = Basic Hydrolysis and/or Neutralization with aqueous NaOH or KOH
DIW = Deionized Water
SU = Synthetic Urine
*mole ratio = moles of crosslinking agent per 100 moles of the ampholytic ion pair and/or comonomer
**g/g = absorbency units of gram aqueous liquid per gram dried polymer Some of the polymers were hydrolyzed and neutralized with a strong base such as aqueous sodium hydroxide or aqueous potassium hydroxide. The degree of hydrolysis or neutralization could be controlled by stoichiometrically limiting the amount of base relative to the amount of amide, nitrile, or carboxylic acid functionalities. A suspension of 1 gram of the polymer in about 20 milliliters of 0.5 molar aqueous sodium hydroxide was heated to 95° C. until a light golden-yellow color was obtained. The mixture was then transferred to a dialysis bag with a molecular weight cut-off of 12,000-14,000 and dialyzed exhaustively against distilled water until the viscous polymer gel had reached pH 7. This viscous polymer gel was then poured into a plastic dish and dried in a forced convection oven at 74° C. The dried polymers were then mechanically blended to a powder.

The dried polymers were then tested for deionized water absorption and synthetic urine absorption. About 1 liter of deionized water or synthetic urine was added to 0.1 to 0.5 gram of the dried polymer and allowed to stand for 24 hours. The polymer was then separated from the excess unabsorbed liquid by screening through

EXAMPLE II

The control data in Table V demonstrates that although commercially available water absorbing materials are highly absorbent to water, they are also dramatically less absorbent to aqueous electrolyte solutions such as salt water and urine. The commercially available water absorbing materials tested include poly(co-acrylamide-co-acrylic acid) grafted onto starch, a commercial acrylamide polymer sold under the trademark "Water Grabber" ® ("Water Grabber" is a trademark of F. P. Products, Inc.), "LUVS" ® diaper absorbent ("LUVS" is a trademark of Procter & Gamble Co.), "Pampers" ® diaper absorbent ("Pampers" is a trademark of Procter & Gamble Co.), and "Favor 960" ® (Stockhausen, Inc.). The best of these known materials absorb up to about 56 grams of urine per gram of absorbing material, and most of the known polymers absorb much less than 40 grams of urine per gram of absorbing material.

TABLE V

Control Data For Commercial Materials

| EXP # | Commercial Material | DIW g/g* | SU g/g* |
|---|---|---|---|
| 1 | COMMERCIAL STARCH-g-POLY(AM-AA) | 345 | 37 |
| 2 | WATER GRABBER ® (AM COPOLYMER) | 440 | 34 |
| 3 | LUVS ® DIAPER ABSORBENT | 191 | 16 |
| 4 | PAMPERS ® DIAPER ABSORBENT | 171 | 12 |
| 5 | FAVOR 960 ® | 369 | 56 | g = graft
AM = Acrylamide
AA = Acrylic Acid
DIW = Deionized Water
SU = Synthetic Urine

*g/g = absorbency units of gram aqueous liquid per gram dried polymer

EXAMPLE III

The homopolymers of the ampholytic ion pair monomers comprising 3-methacrylamidopropyldimethylammonium 2-acrylamido-2-methylpropane sulfonate (MPDMA/AMPS) ("AMPS" is a trademark of Lubrizol Corporation for 2-acrylamido-2-methylpropane sulfonic acid) or 3-methacrylamidopropyldimethylammonium 2-methacryloyloxyethane sulfonate (MPDMA/MES) with 0.05 weight percent methylene-bis-acrylamide cross linking agent was tested for these absorbency to deionized water and synthetic urine. The absorbency of homopolymers is very poor. See Table VI.

TABLE VI

Control Data For Ion Pair Homopolymer

| EXP # | MPDMA/AMPS MOLE PERCENT | MPDMA/MES MOLE PERCENT | LINK mole ratio* | DIW g/g** | SU g/g** |
|---|---|---|---|---|---|
| 319 | 100 | — | 0.05 | 10 | 23 |
| 100 | — | 100 | 0.05 | 12 | 17 |

MPDMA/AMPS = 3-methacrylamidopropyldimethylammonium cation 2-acrylamido-2-methylpropane sulfonate anion
MPDMA/MES = 3-methacrylamidopropyldimethylammonium cation 2-methacryloyloxyethane sulfonate anion
LINK = Methylene-bis-acrylamide Crosslinking Agent
DIW = Deionized Water
SU = Synthetic Urine
*mole ratio = moles of crosslinking agent per 100 moles of the ampholytic ion pair and/or comonomer
**g/g = absorbency units of gram aqueous liquid per gram dried polymer

EXAMPLE IV

The control data in Table VII demonstrates that although the known ampholytic ion pair 3-methacrylamidopropyltrimethylammonium 2-acrylamido-2-methylpropane sulfonate (MPTMA/AMPS) copolymerized with acrylamide is highly absorbent to deionized water, it is dramatically less absorbent to aqueous electrolyte solutions such as salt water, brine, and urine. The absorbency to synthetic urine is about the same as for the better of the known polymers and commercial materials. The MPTMA/AMPS-acrylamide copolymer also has been grafted onto starch using ceric ion or cobalt-60 irradiation. These starch grafted copolymers are poorly absorbent to deionized water, and only slightly more absorbent to synthetic urine. The better of these known polymers absorbs up to about 56 grams of urine per gram of polymer, but the rest absorb less than 30 grams of urine per gram of polymer.

TABLE VII

Control Data For Known MPTMA/AMPS-Acrylamide Copolymers

| EXP # | MPTMA/AMPS MOLE PERCENT | AM | LINK mole ratio* | Starch | XOH | DIW g/g** | SU g/g** |
|---|---|---|---|---|---|---|---|
|  | 10 | 90 | — | — | NO | soluble | |
| 87 | 10 | 90 | 0.20 | — | YES | 428 | 56 |
| *** | 8.56 | 27.30 | — | 64.86 | NO | 9.83 | 16.21 |
| *** | 8.98 | 41.76 | — | 49.26 | NO | 11.54 | 16.62 |
| *** | 15.01 | 64.96 | — | 20.03 | NO | 14.11 | 29.45 |

MPTMA/AMPS = 3-methacrylamidopropyldimethylammonium cation/2-acrylamido-2-methylpropane sulfonate anion
AM = Acrylamide
LINK = Methylene-bis-acrylamide Crosslinking Agent
XOH = Basic Hydrolysis and/or Neutralization with aqueous NaOH or KOH
DIW = Deionized Water
SU = Synthetic Urine
*mole ratio = mole crosslinking agent per 100 mole of the ampholytic ion pair monomer and the comonomers
**g/g = absorbency units of gram aqueous liquid per gram dried polymer
***J. C. Salamone, E. L. Rodriguez, K. C. Lin, L. Quach, A. C. Watterson and I. Ahmed, Polymer 26, 1234-38 (1985).

EXAMPLE V

The polymers of the present invention were prepared according to the method described in Example 1, except that the inventive polymers were prepared by mixing the monomers in the proportions given in Tables VIII.

The inventive polymers were tested for absorbency to deionized water and synthetic urine. The tested polymers of the present invention comprise polymers formed by the copolymerization of an effective amount of the components listed in the following table to produce polymers highly absorbent to aqueous electrolyte solutions.

Some of these inventive polymers in this example which contain an olefinic comonomer with amide, nitrile, carboxylic acid, or sulfonic acid functionalities or crosslinking agent with amide, nitrile, carboxylic acid, or sulfonic acid functionalities were hydrolyzed and neutralized with an aqueous base such as aqueous sodium hydroxide or aqueous potassium hydroxide.

TABLE VIII

Experimental Data For Inventive MPDMA/AMPS Polymers

| EXP # | MPDMA/AMPS | AM | AN | AA | X-AA | LINK mole ratio* | XOH | DIW g/g** | SU |
|---|---|---|---|---|---|---|---|---|---|
| | MOLE PERCENT | | | | | | | | |
| 415 | 5 | 95 | — | — | — | 0.05 | YES | 429 | 60 |
| 416 | 10 | 90 | — | — | — | 0.05 | YES | 488 | 71 |
| 417 | 15 | 85 | — | — | — | 0.05 | YES | 516 | 82 |
| 418 | 20 | 80 | — | — | — | 0.05 | YES | 598 | 91 |
| 411 | 5 | — | 95 | — | — | 0.10 | YES | 600 | 98 |
| 412 | 10 | — | 90 | — | — | 0.10 | YES | 551 | 89 |
| 413 | 15 | — | 85 | — | — | 0.10 | YES | 786 | 94 |
| 414 | 20 | — | 80 | — | — | 0.10 | YES | 724 | 117 |
| 309 | 1.4 | 20.3 | — | — | 78.3 | 0.05 | NO | 662 | 72 |
| 310 | 2.8 | 20.7 | — | — | 76.5 | 0.05 | NO | 674 | 76 |
| 236 | 3 | 13 | — | — | 84 | 0.05 | NO | 666 | 72 |
| 232 | 3 | 13 | — | — | 84 | 0.05 | NO | 780 | 71 |
| 237 | 6 | 13 | — | — | 81 | 0.05 | NO | 700 | 84 |
| 327 | 6 | 20 | — | — | 74 | 0.05 | NO | 642 | 80 |
| 233 | 6 | 13 | — | — | 81 | 0.05 | NO | 768 | 83 |
| 238 | 10 | 13 | — | — | 77 | 0.05 | NO | 782 | 83 |
| 311 | 10 | 20 | — | — | 70 | 0.05 | NO | 494 | 70 |
| 239 | 15 | 13 | — | — | 72 | 0.05 | NO | 542 | 72 |
| 101 | 1 | — | — | — | 99 | 0.05 | NO | 747 | 90 |
| 102 | 3 | — | — | — | 97 | 0.05 | NO | 832 | 93 |
| 103 | 6 | — | — | — | 94 | 0.05 | NO | 679 | 77 |
| 104 | 10 | — | — | — | 90 | 0.05 | NO | 781 | 79 |
| 105 | 25 | — | — | — | 75 | 0.05 | NO | 620 | 54 |

MPDMA/AMPS = 3-methacrylamidopropyldimethylammonium cation/2-acrylamido-2-methylpropane sulfonate anion
AM = Acrylamide
AN = Acrylonitrile
AA = Acrylic Acid
X-AA = Alkali Salt of Acrylic Acid (Acrylate)
LINK = Methylene-bis-acrylamide Crosslinking Agent
XOH = Basic Hydrolysis and/or Neutralization with aqueous NaOH or KOH
DIW = Deionized Water
SU = Synthetic Urine
*mole ratio = mole crosslinking agent per 100 moles of the ampholytic ion pair monomer and the comonomer
**g/g = absorbency units of gram aqueous liquid per gram dried polymer

TABLE IX

Experimental Data For Inventive MPDMA/MES Polymers

| EXP # | MPDMA/MES | AM | AN | AA | X-AA | LINK mole ratio* | XOH | DIW g/g** | SU |
|---|---|---|---|---|---|---|---|---|---|
| | MOLE PERCENT | | | | | | | | |
| 95 | 1 | — | — | — | 99 | 0.05 | NO | 638 | 88 |
| 96 | 3 | — | — | — | 97 | 0.05 | NO | 645 | 96 |
| 97 | 6 | — | — | — | 94 | 0.05 | NO | 483 | 84 |
| 98 | 10 | — | — | — | 90 | 0.05 | NO | 401 | 73 |
| 99 | 25 | — | — | — | 75 | 0.05 | NO | 386 | 75 |

MPDMA/AMPS = 3-methacrylamidopropyldimethylammonium cation/2-acrylamido-2-methylpropane sulfonate anion
AM = Acrylamide
AN = Acrylonitrile
AA = Acrylic Acid
X-AA = Alkali Salt of Acrylic Acid (Acrylate)
LINK = Methylene-bis-acrylamide Crosslinking Agent
XOH = Basic Hydrolysis and/or Neutralization with aqueous NaOH or KOH
DIW = Deionized Water
SU = Synthetic Urine
*mole ratio = mole crosslinking agent per 100 moles of the ampholytic ion pair monomer and the comonomer
**g/g = absorbency units of gram aqueous liquid per gram dried polymer The data in Tables VIII and IX demonstrates that these polymers exhibit significantly improved absorbency to aqueous electrolyte solutions such as urine over the absorbency of the known polymers listed in Table IV, the commercially available materials listed in Table V, the crosslinked MPDMA/sulfonate homopolymers listed in Table VI, and the analogous crosslinked MPTMA/AMPS-acrylamide copolymers listed in Table VII.

The absorbency of these polymers to urine is highly unexpected in view of the fact that the homopolymers of MPDMA/sulfonate with 0.05 weight percent crosslinking agent only absorb about 20 grams of synthetic urine per gram of the polymer. See Table VI. This demonstrates that the monomers when combined into the polymers of the present invention act synergistically to increase the absorbency of the polymers to aqueous liquids such as salt water and urine.

Taking an absorbency of about 56 grams of synthetic urine per gram of polymer as about the best of the known polymers, the preferred polymers of the present invention exceed this absorbency to urine by 25–63 percent (70–91 grams synthetic urine per gram of inventive polymer, Table VIII, compared to 56 grams urine per gram for the best known materials, Tables IV, V, VI, and VII) without sacrificing absorbency to deionized water. These improved absorbencies translate into large savings in the quantity of polymer required and large savings to the consumer.

Reasonable variations can be made in view of the foregoing disclosure without departing from the spirit or scope of the present invention.

We claim:

1. An article of manufacture selected from the group consisting of a paper towel and a disposable diaper containing therein a polymer formed by the copolymerization of an effective amount of each of the following components to produce a polymer which is highly absorbent to aqueous electrolyte solutions:
   (a) an ampholytic ion pair monomer comprising
      (i) an ammonium cation 3-methacrylamidopropyldimethylammonium and
      (ii) a sulfonate anion selected from the group consisting of 2-acrylamido-2-methylpropane sulfonate, 2-methacryloyloxyethane sulfonate, vinyl sulfonate, styrene sulfonate and combinations of two or more thereof;
   (b) at least one comonomer selected from the group consisting of acrylamide, methacrylamide, acrylonitrile, acrylic acid, methacrylic acid, alkali salts of acrylic acid, alkali salts of methacrylic acid, N-vinyl-2-pyrrolidone and combinations of two or more thereof; and
   (c) at least one crosslinking agent which has at least two polymerizable olefinic functionalities wherein each of the olefinic functionalities is suitable for crosslinking.

2. An article of manufacture in accordance with claim 1 wherein the crosslinking agent is selected from the group consisting of N,N-diallylmethacrylamide, diallylamine, N,N-bisacrylamidoacetic acid, N,N'-bisacrylamidoacetic acid methylester, N,N'-methylenebisacrylamide N,N-benzylidenebisacrylamide, allylacrylate, diisopropenylbenzene, diallyl succinate, ethylene glycol diacrylate, diallylacrylamide, divinylbenzene, and combinations of two or more thereof.

3. An article of manufacture in accordance with claim 2 wherein the crosslinking agent comprises methylene-bis-acrylamide.

4. An article of manufacture in accordance with claim 1 wherein the polymer is at least partially hydrolyzed.

5. An article of manufacture in accordance with claim 1 wherein the polymer is at least partially neutralized.

6. An article of manufacture in accordance with claim 1 wherein the comonomer is selected from the group consisting of acrylamide, acrylonitrile, acrylic acid, alkali salts of acrylic acid, and any combination of two or more thereof.

7. An article of manufacture in accordance with claim 6 wherein the comonomer is acrylamide.

8. An article of manufacture in accordance with claim 7 wherein the polymer comprises a polymer formed by the polymerization of:
   (a) in the range of about 10 mole percent to about 30 mole percent of the ampholytic ion pair monomer;
   (b) in the range of about 70 mole percent to about 90 mole percent of the comonomer, wherein the total amount of the ampholytic ion pair monomer and the comonomer equals 100 mole percent; and
   (c) in the range of about 0.01 mole percent to about 0.3 mole percent of the crosslinking agent per 100 moles of the ampholytic ion pair monomer and the comonomer.

9. An article of manufacture in accordance with claim 8 wherein the polymer is formed by the polymerization of:
   (a) in the range of about 10 mole percent to about 25 mole percent of the ampholytic ion pair monomer;
   (b) in the range of about 75 mole percent to about 90 mole percent of the comonomer, wherein the total amount of the ampholytic ion pair monomer and the comonomer equals 100 mole percent; and
   (c) in the range of about 0.01 mole percent to about 0.2 mole percent of the crosslinking agent per 100 moles of the ampholytic ion pair monomer and the comonomer.

10. An article of manufacture in accordance with claim 7 wherein the sulfonate anion is selected from the group consisting of 2-acrylamido-2-methylpropane sulfonate and 2-methacryloyloxyethane sulfonate.

11. An article of manufacture in accordance with claim 10 wherein the polymer is formed by the polymerization of:
    (a) in the range of about 10 mole percent to about 30 mole percent of the ampholytic ion pair monomer;
    (b) in the range of about 70 mole percent to about 90 mole percent of the comononer, wherein the total amount of the ampholytic ion pair monomer and the comonomer equals 100 mole percent; and
    (c) in the range of about 0.01 mole percent to about 0.2 mole percent of the crosslinking agent per 100 moles of the ampholytic ion pair monomer and the comonomer.

12. An article of manufacture in accordance with claim 11 wherein the polymer is formed by the polymerization of:
    (a) in the range of about 10 mole percent to about 25 mole percent of the ampholytic ion pair monomer;
    (b) in the range of about 75 mole percent to about 90 mole percent of the comonomer, wherein the total amount of the ampholytic ion pair monomer and the comonomer equals 100 mole percent; and
    (c) in the range of about 0.01 mole percent to about 0.1 mole percent of the crosslinking agent per 100 moles of the ampholytic ion pair monomer and the comonomer.

13. An article of manufacture in accordance with claim 6 wherein the comonomer is acrylonitrile.

14. An article of manufacture in accordance with claim 13 wherein the polymer comprises a polymer formed by the polymerization of:
    (a) in the range of about 3 mole percent to about 35 mole percent of the ampholytic ion pair monomer;
    (b) in the range of about 65 mole percent to about 97 mole percent of the comonomer, wherein the total amount of the ampholytic ion pair monomer and the comonomer equals 100 mole percent; and
    (c) in the range of about 0.01 mole percent to about 0.3 mole percent of the crosslinking agent per 100 moles of the ampholytic ion pair monomer and the comonomer.

15. An article of manufacture in accordance with claim 14 wherein the polymer is formed by the polymerization of:
    (a) in the range of about 5 mole percent to about 25 mole percent of the ampholytic ion pair monomer;
    (b) in the range of about 75 mole percent to about 95 mole percent of the comonomer, wherein the total amount of the ampholytic ion pair monomer and the comonomer equals 100 mole percent; and
    (c) in the range of about 0.01 mole percent to about 0.2 mole percent of the crosslinking agent per 100 moles of the ampholytic ion pair monomer and the comonomer.

16. An article of manufacture in accordance with claim 13 wherein the sulfonate anion is selected from the group consisting of 2-acrylamido-2-methylpropane sulfonate and 2-methacryloyloxyethane sulfonate.

17. An article of manufacture in accordance with claim 16 wherein the polymer is formed by the polymerization of:
   (a) in the range of about 3 mole percent to about 35 mole percent of the ampholytic ion pair monomer;
   (b) in the range of about 65 mole percent to about 97 mole percent of the comonomer, wherein the total amount of the ampholytic ion pair monomer and the comonomer equals 100 mole percent; and
   (c) in the range of about 0.01 mole percent to about 0.2 mole percent of the crosslinking agent per 100 moles of the ampholytic ion pair monomer and the comonomer.

18. An article of manufacture in accordance with claim 17 wherein the polymer is formed by the polymerization of:
   (a) in the range of about 5 mole percent to about 25 mole percent of the ampholytic ion pair monomer;
   (b) in the range of about 75 mole percent to about 95 mole percent of the comonomer, wherein the total amount of the ampholytic ion pair monomer and the comonomer equals 100 mole percent; and
   (c) in the range of about 0.01 mole percent to about 0.1 mole percent of the crosslinking agent per 100 moles of the ampholytic ion pair monomer and the comonomer.

19. An article of manufacture in accordance with claim 6 wherein the comonomer is a alkali salt of acrylic acid.

20. An article of manufacture in accordance with claim 19 wherein the polymer comprises a polymer formed by the polymerization of:
   (a) in the range of about 1 mole percent to about 30 mole percent of the ampholytic ion pair monomer;
   (b) in the range of about 70 mole percent to about 99 mole percent of the comonomer, wherein the total amount of the ampholytic ion pair monomer and the comonomer equals 100 mole percent; and
   (c) in the range of about 0.01 mole percent to about 0.3 mole percent of the crosslinking agent per 100 moles of the ampholytic ion pair monomer and the comonomer.

21. An article of manufacture in accordance with claim 26 wherein the polymer is formed by the polymerization of:
   (a) in the range of about 1 mole percent to about 10 mole percent of the ampholytic ion pair monomer;
   (b) in the range of about 90 mole percent to about 99 mole percent of the comonomer, wherein the total amount of the ampholytic ion pair monomer and the comonomer equals 100 mole percent; and
   (c) in the range of about 0.01 mole percent to about 0.2 mole percent of the crosslinking agent per 100 moles of the ampholytic ion pair monomer and the comonomer.

22. An article of manufacture in accordance with claim 19 wherein the sulfonate anion is 2-acrylamido-2-methylpropane sulfonate.

23. An article of manufacture in accordance with claim 22 wherein the polymer is formed by the polymerization of:
   (a) in the range of about 1 mole percent to about 15 mole percent of the ampholytic ion pair monomer;
   (b) in the range of about 85 mole percent to about 99 mole percent of the comonomer, wherein the total amount of the ampholytic ion pair monomer and the comonomer equals 100 mole percent; and
   (c) in the range of about 0.01 mole percent to about 0.2 mole percent of the crosslinking agent per 100 moles of the ampholytic ion pair monomer and the comonomer.

24. An article of manufacture in accordance with claim 23 wherein the polymer is formed by the polymerization of:
   (a) in the range of from about 1 mole percent to about 10 mole percent of the ampholytic ion pair monomer;
   (b) in the range of from about 90 mole percent to about 99 mole percent of the comonomer, wherein the total amount of the ampholytic ion pair monomer and the comonomer equals 100 mole percent; and
   (c) in the range of about 0.01 mole percent to about 0.1 mole percent of the crosslinking agent per 100 moles of the ampholytic ion pair monomer and the comonomer.

25. An article of manufacture in accordance with claim 19 wherein the sulfonate anion is 2-methacryloyloxyethane sulfonate.

26. An article of manufacture in accordance with claim 25 wherein the polymer is formed by the polymerization of:
   (a) in the range of from about 1 mole percent to about 25 mole percent of the ampholytic ion pair monomer;
   (b) in the range of from about 75 mole percent to about 99 mole percent of the comonomer, wherein the total amount of the ampholytic ion pair monomer and the comonomer equals 100 mole percent; and
   (c) in the range of about 0.01 mole percent to about 0.2 mole percent of the crosslinking agent per 100 moles of the ampholytic ion pair monomer and the comonomer.

27. An article of manufacture in accordance with claim 26 wherein the polymer is formed by the polymerization of:
   (a) in the range of from about 1 mole percent to about 6 mole percent of the ampholytic ion pair monomer;
   (b) in the range of from about 94 mole percent to about 99 mole percent of the comonomer, wherein the total amount of the ampholytic ion pair monomer and the comonomer equals 100 mole percent; and
   (c) in the range of about 0.01 mole percent to about 0.1 mole percent of the crosslinking agent per 100 moles of the ampholytic ion pair monomer and the comonomer.

28. An article of manufacture in accordance with claim 6 wherein the comonomer is a combination of acrylamide and alkali salt of acrylic acid.

29. An article of manufacture in accordance with claim 28 wherein the polymer comprises a polymer formed by the polymerization of:
   (a) in the range of about 1 mole percent to about 20 mole percent of the ampholytic ion pair monomer;
   (b) in the range of about 10 mole percent to about 25 mole percent of the acrylamide comonomer;
   (c) in the range of about 55 mole percent to about 89 mole percent of the alkali salt of acrylic acid comonomer, wherein the total amount of the ampholytic ion pair monomer and the comonomer equals 100 mole percent; and (d) in the range of about 0.01 mole percent to about 0.3 mole percent of the crosslinking agent per 100 moles of the ampholytic ion pair monomer and the comonomer.

30. An article of manufacture in accordance with claim 29 wherein the polymer is formed by the polymerization of:
 (a) in the range of about 1.5 mole percent to about 15 mole percent of the ampholytic ion pair monomer;
 (b) in the range of about 10 mole percent to about 20 mole percent of the acrylamide comonomer;
 (c) in the range of about 65 mole percent to about 88.5 mole percent of the alkali salt of acrylic acid comonomer, wherein the total amount of the ampholytic ion pair monomer and the comonomer equals 100 mole percent; and
 (d) in the range of about 0.01 mole percent to about 0.2 mole percent of the crosslinking agent per 100 moles of the ampholytic ion pair monomer and the comonomer.

31. An article of manufacture in accordance with claim 28 wherein the sulfonate anion is selected from the group consisting of 2-acrylamido-2-methylpropane sulfonate and 2-methacryloyloxyethane sulfonate.

32. An article of manufacture in accordance with claim 31 wherein the polymer is formed by the polymerization of:
 (a) in the range of about 1.5 mole percent to about 15 mole percent of the ampholytic ion pair monomer;
 (b) in the range of about 10 mole percent to about 21 mole percent of the acrylamide comonomer;
 (c) in the range of about 64 mole percent to about 88.5 mole percent of the alkali salt of acrylic acid comonomer, wherein the total amount of the ampholytic ion pair monomer and the comonomer equals 100 mole percent; and
 (d) in the range of about 0.01 mole percent to about 0.2 mole percent of the crosslinking agent per 100 moles of the ampholytic ion pair monomer and the comonomer.

33. An article of manufacture in accordance with claim 32 wherein the polymer is formed by the polymerization of:
 (a) in the range of about 6 mole percent to about 10 mole percent of the ampholytic ion pair monomer;
 (b) in the range of about 10 mole percent to about 15 mole percent of the acrylamide comonomer;
 (c) in the range of about 75 mole percent to about 84 mole percent of the alkali salt of acrylic acid comonomer, wherein the total amount of the ampholytic ion pair monomer and the comonomer equals 100 mole percent; and
 (d) in the range of about 0.01 mole percent to about 0.1 mole percent of the crosslinking agent per 100 moles of the ampholytic ion pair monomer and the comonomer.

* * * * *